United States Patent [19]

Eiceman et al.

[11] Patent Number: 4,777,363

[45] Date of Patent: Oct. 11, 1988

[54] ION MOBILITY SPECTROMETER

[75] Inventors: Gary A. Eiceman; Craig S. Leasure, both of Las Cruces, N. Mex.

[73] Assignee: Research Corporation Technologies, Inc., New York, N.Y.

[21] Appl. No.: 902,257

[22] Filed: Aug. 29, 1986

[51] Int. Cl.$^4$ ............................................. B01D 59/44
[52] U.S. Cl. ..................................... 250/286; 250/287
[58] Field of Search .............. 250/281, 282, 286, 287

[56] References Cited

U.S. PATENT DOCUMENTS

| | | | |
|---|---|---|---|
| 3,626,181 | 12/1971 | Wernlund | 250/287 |
| 3,845,301 | 10/1974 | Wernlund et al. | 250/286 |
| 4,238,678 | 12/1980 | Castleman et al. | 250/287 |
| 4,378,499 | 3/1983 | Spangler et al. | 250/286 |
| 4,527,059 | 7/1985 | Benninghoven et al. | 250/287 |
| 4,551,624 | 11/1985 | Spangler et al. | 250/287 |
| 4,597,299 | 7/1986 | Campbell et al. | 250/286 |

*Primary Examiner*—Bruce C. Anderson
*Attorney, Agent, or Firm*—Scully, Scott, Murphy & Presser

[57] ABSTRACT

An atmospheric ion mobility spectrometer including a spectrometer tube having a shutter grid defining a reaction region and a drift chamber. The tube includes an inlet at the end of the drift chamber opposite the shutter grid in communication with ambient air that allows the air to be introduced into the tube. The air acts as the sample, carrier gas and drift gases within the IMS.

14 Claims, 3 Drawing Sheets

ION MOBILITY SPECTROMETER

BACKGROUND OF THE INVENTION

1. Field of the Invention

This invention is generally directed to an ion mobility spectrometer and more particularly to a spectrometer for sampling the atmosphere for use as a portable device for detecting contaminants in the air.

2. Background of the Invention

Ion mobility spectrometry has been developing as a technique for detecting contaminants in gas samples for 25 to 30 years. Ion movement is dependent upon mobility and is therefore related to the size and charge of the ions. Primarily only singly charged ions are observed with an IMS. The IMS device consists of an atmospheric pressure ionizer coupled to a drift tube spectrometer. Sample molecules that are ionized by ion-molecule reactions enter a drift region where they are separated according to mobility. A radioactive source, usually Ni-63, ionizes a carrier gas that is introduced into reaction region to form reactant ions. In the presence of the vapor sample having the contaminant to be identified, the reactant ions undergo ion-molecule reactions with the sample molecules to form product ions. An electric field gradient present throughout the tube causes the product ions to be introduced into the drift region.

A shutter grid separating the reaction region from the drift region interrupts the flow of ions during this process. The shutter grid is an array of parallel wires that are alternately biased so that the application of equal potentials to alternate wires will permit the product ions to pass to the drift region, while unequal potentials will deflect the arriving ions and prevent their passage into the drift region. Typically, the shutter grid is pulsed every 40 milliseconds to transmit the ions into the drift region. Upon entering the drift region the ions travel toward a collector plate under the influence of the electric field gradient.

A drift gas is introduced into the drift region to quench any remaining reactions and to collide with the product ions to produce a drift velocity unique for each contaminant. The ions arriving at the collector plate are measured as current peaks separated by the arrival time. A detector analyzes the current peaks to provide a mobility signature to permit the identification of the presence of a particular contaminant.

The prior art ion mobility spectrometers (IMS) have major disadvantages for direct application in atmospheric sensing. The sample vapor introduced into the present IMS tubes must be considerably manipulated. In addition, the prior IMS tubes utilize a carrier gas that must be purified air or prepurified nitrogen. If ambient air is used as the carrier gas, the ammonia and water components of the air alter the identity of the reactant ions that may interfere with the IMS response to the sample. Thus, large pressured tanks are required to purify and introduce the carrier gas into the reaction region. Moreover, the drift gas must also be a purified gas that is introduced into the drift region from the pressure tanks. Provision is made to release the purified carrier and drift gases near the shutter grid.

One prior art IMS system which uses ambient air as the carrier gas is disclosed in Spangler et al. Developments In Ion Mobility Spectrometry, 23 ISA Transactions No. 1, 17-28 (1984). The Spangler et al. IMS tube utilizes a specially designed membrane inlet that allows a continuous recycled nitrogen stream with sample to be drawn across the external surface of the membrane while the carrier gas flows across the interior surface of the membrane. The membrane excludes such elements as ammonia, water and nitrogen oxide. However, this system still requires a means for purifying the carrier and drift gases, thus not overcoming the limitation of the prior art IMS tubes of being impractical for portable contaminant testing.

SUMMARY OF THE INVENTION

In accordance with the present invention there is provided an ion mobility spectrometer having a substantially cylindrical tube in which there is a shutter grid defining a reaction region and a drift chamber within the tube. The drift chamber includes the plurality of metallic rings that extend from the shutter grid to a collector plate at the opposite end of the drift chamber. An inlet in communication with ambient air is provided at the end of the drift chamber having the collector plate for the introduction of ambient air into the tube. A means for detecting the drift velocity of product ions within the drift chamber is coupled to the collector plate. Means for applying a potential gradient across the tube and means for applying a potential gradient across the shutter grid are provided. A radioactive source emits radioactive particles into the reaction region to form the reactant ions which react with the sample to form product ions. Alternatively a photoionization source such as a hydrogen discharge lamp or a laser may be used to produce product ions directly from the sample. In addition, a means for causing ambient air to enter the inlet, travel through the drift tube and be released through a drift gas exit in the reaction region is also provided. The present invention provides for the ambient air to act as the sample and the carrier gases that undergoes the ion-molecular reactions in the reaction chamber that produces the product ions. The ambient air also acts as the drift gas that collides with the product ions within the drift region to produce the drift velocity. The applicants' invention provides a continuous sensing IMS tube that samples atmospheric compounds with a high sensitivity and selectivity.

Air samples are introduced into the IMS tube through the drift gas inlet as opposed to the prior art devices that introduce the samples near the reaction region. The IMS drift tube is sealed from external atmosphere and a vacuum is applied to the drift gas exit using a small vacuum pump. With the vacuum pump on, air from the external atmosphere will be drawn to the IMS for detection of trace substances in the air sample. In a preferred embodiment, two gas lines are attached to the drift gas inlet, one with an inline molecular sieve cartridge to filter and purify the air and the second with no filter to introduce actual air sample. By means of a variable flow controller on the first line, a variable and known gas flow of air sample will be allowed into the IMS. Thus, the need for positive pressure gases or air sampling inlets in the IMS are eliminated.

DETAILED DESCRIPTION OF THE INVENTION

Figure 1:
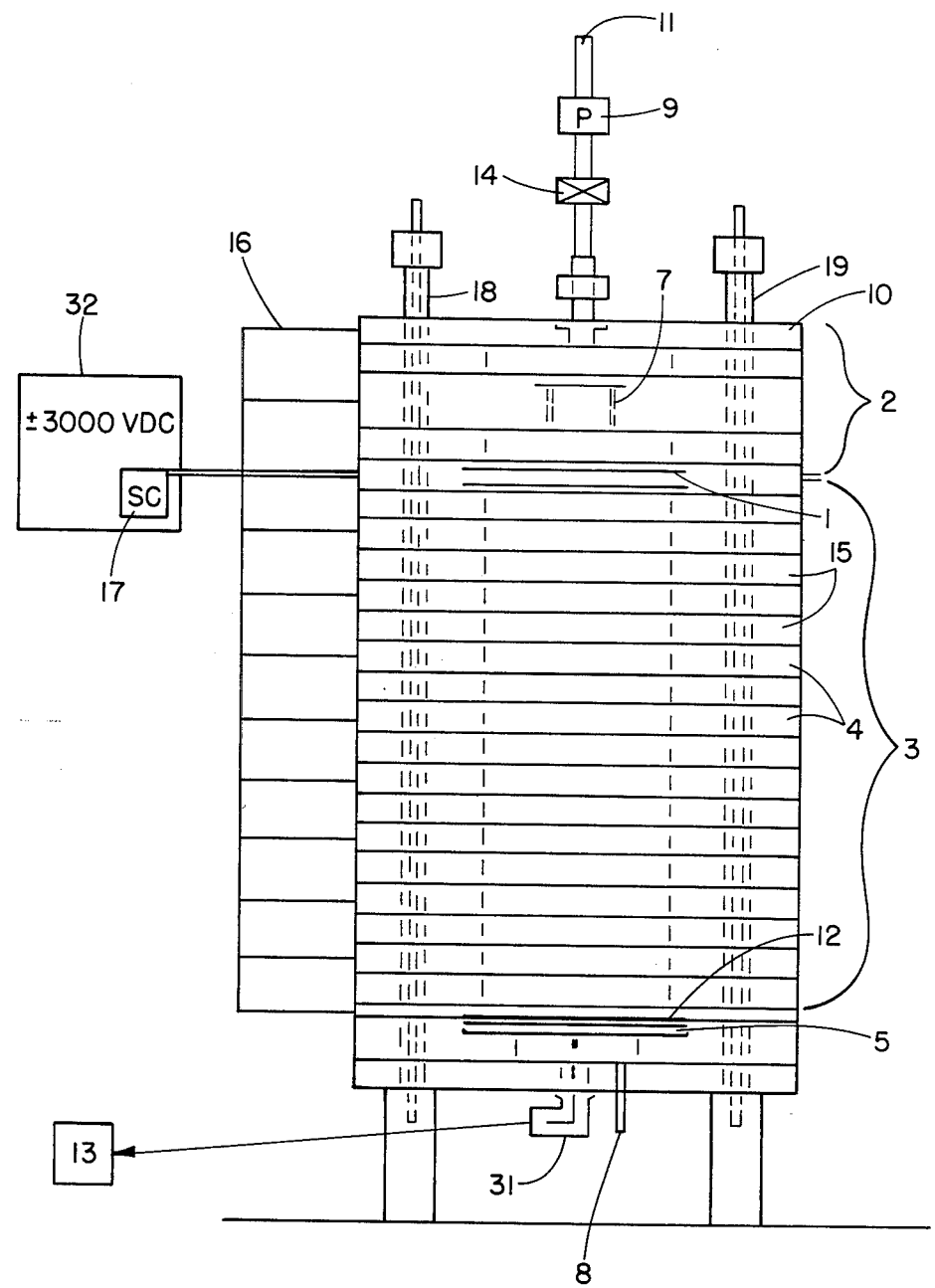
FIG. 1 is a schematic diagram of the ion mobility spectrometer of the present invention.

Referring now to the drawing, FIG. 1 shows the ion mobility spectrometer of the present invention having a substantially cylindrical spectrometer tube housing the device. Within the tube is a shutter grid 1 defining a reaction region 2 and a drift chamber 3. The drift chamber comprises a stack of metallic cylindrical rings two of which are illustrated at 4 in FIG. 1 that extend from the shutter grid to one end of the drift tube thereby forming a segmented tube. The segmented tube also includes a plurality of intervening insulating rings, two of which are illustrated at 15 in FIG. 1. The insulating rings 15 are placed between the metallic rings 4, and are held together by spring-loaded compression clamps that press the stack together alone support rods 18, 19 as illustrated in FIG. 1. A collector plate 5 is positioned at the end of the drift chamber 3 opposite to the shutter grid 1. A detector means 13 is coupled to the collector plate 5 at coaxial coupling means 31 for detecting the drift velocity of ions arriving at the collector. A means is provided for applying a potential gradient across the tube. The potential gradient is preferably between 200-300 volts per cm. It is possible to use a smaller gradient but not to use a much higher gradient because the air could then be ionized. In FIG. 1 the means is a voltage source 32 which creates a 221 volt per cm potential gradient. The highest potential is at the wire 16 which is connected to the repeller plate 10. In addition, a shutter control means 17 is also provided for applying a potential gradient to the shutter grid 1.

An ionization source 7 for emitting radioactive molecules is located within the reaction region 2. The other end of the drift tube near the collector plate 5 includes an inlet 8 in communication with the atmospheric air for receiving the air and sample into the tube. An in-line pump means 9 is provided for drawing air from the inlet, through the drift chamber 3 and reaction region 2. Humidity will only effect the drift gas if organics such as alcohols, aldehydes, ketones or amines are present in the air. In contrast mobility spectra for aromatic compounds, polycyclic aromatic hydrocarbons, chlorinated hydrocarbons and others are not effected substantially by water in the drift gas. The air drawn in through the inlet 8 acts as the sample and carrier gas that undergoes the ion-molecular reactions in the reaction region 2 to produce product ions and also the drift gas that collides with the product ions entering the drift chamber 3 to produce the drift velocity.

The ion mobility spectrometer of the present invention is of a uniflow design wherein the air samples are introduced into the tube through the drift gas inlet 8 as opposed to conventional prior art ion mobility spectrometers in which the sample is introduced near the reaction region 2. The IMS drift tube is of a closed-tube design wherein the tube is sealed from external atmospheres. In the illustrative embodiment shown in FIG. 1, the segmented tube IMS includes stainless steel drift rings 4 separated by Macor insulators 15 which are secured by spring-loaded compression clamps acting along the axis of supports 18, 19. A repeller plate 10 is provided at the end of the tube having the drift gas exit 11 and an aperture grid 12 is coupled to the collector plate 5. The IMS of the present invention is constructed for using air as the drift gas and as the carrier gas containing vapors from solid or liquid samples or as a gaseous sample. The tubes are small and simple. The IMS is pneumatically sealed with a pump 9 on the repeller 10 end.

In one embodiment, the drift tube is hermetically sealed from external atmospheres by the placement of o-rings between segments of the drift tube rings. Alternatively, a glass tube is provided throughout the inner diameter of the segmented drift tube. The hermetically sealed drift tube will reduce or eliminate contamination from external atmospheres and permit the IMS to be used for sample introduction through the drift gas inlet 8. The lining for the IMS drift tube may also be made of teflon or any other material that allows an electric field to penetrate into the drift tube. The lining may be utilized with either a segmented or continuous tube design. The lining eliminates diffusion of contaminants between the segments of drift tube which cause memory effects due to contamination of the tube from sample to sample. The inner lining also prevents the drift gas and sample from coming in direct contact with the individual pieces of the drift tube that decompose thereby causing contamination of the device. Accordingly, this embodiment will allow the detection of corrosive or reactive gases without problems due to materials.

The pump means 9 located at the drift gas exit 11 may also be a vacuum pump on the repeller plate 10 rather than as illustrated in FIG. 1. When the vacuum pump 9 is actuated, air from the external atmosphere will be drawn through the IMS for detection of trace substances in the air sample. The line to the vacuum pump may contain an in-line molecular sieve cartridge 14 to prevent corrosive ions from getting into the vacuum pump. In a preferred embodiment the molecular sieve catridge 14 is 5 Angstrom in size. The flow rate of the pump is preferably between 100 ml/min and 10 l/min. The pump means is any pump which can be utilized with a gaseous fluid. Commercially available rotary or vacuum pumps are suitable pump means. In one embodiment the Spectrex minipump with a small pulsing diaphragm is used as the pump means. The air pressure differential between the end of the drift tube containing the repeller plate 10 and ambient atmosphere at a pump rate of 300-800 ml/min is less than 1 mm of mercury.

Figure 2:
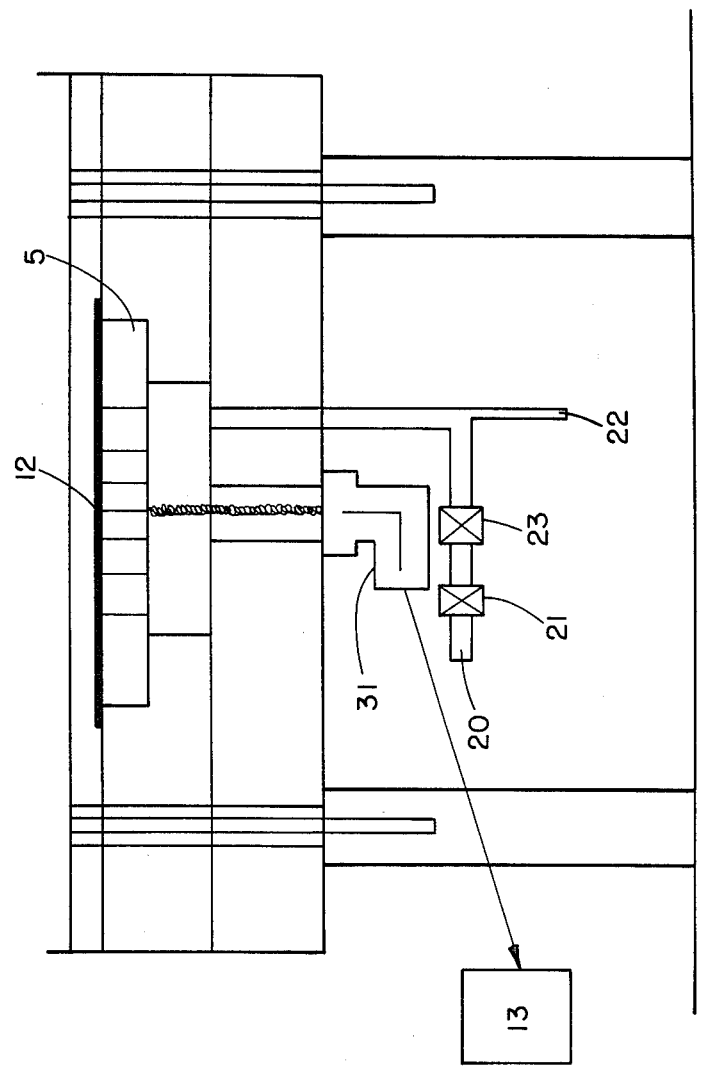
FIG. 2 is a schematic diagram of the lower portion of FIG. 1 wherein the sample and drift gas entrance comprises a sample inlet and a drift gas inlet containing a molecular seive cartridge.

In a preferred embodiment, as illustrated in FIG. 2, two gas lines, are be attached to the drift gas inlet, a first line 20 having an inline molecular sieve cartridge 21 to filter and purify the air and a second line 22 with no filter to introduce actual air sample into the IMS. The molecular sieve cartridge 21 in the preferred embodiment is 5 Angstrom in size. A variable flow controller 23 on the first line permits a variable and known gas flow (10 ml/min-200 ml/min) of air sample through the IMS. The air sample preferably has a flow rate between 10 and 100 ml/min. The drift gas preferably has a flow rate between 300 and 800 ml/min. This design will eliminate need for positive pressure gas use or air sampling inlets in the IMS.

The ion mobility spectrometer of the present invention by using the ambient or external atmosphere for all sample and drifts gases introduced into the IMS tube uniquely permits the IMS to be utilized as an atmospheric sensor for the separation and detection of trace substances in air. As an atmospheric sensor, toxics and other important substances may be detected, such as pesticides, explosive products and drugs.

As illustrated in FIG. 1, the repeller plate 10 is at the highest potential in the gradient. The repeller plate 10 is supplied with 1,000 to 5,000 volts. The repeller plate aids in directing the ions into the drift chamber. Repeller plates are known in the art and have been described in Baim, M. A.; Hill, H. H., Jr., Anal. Chem., 1982 54, 38 and Baim, M. A.; Eatherton, R. L.; Hill, H. H., Jr., Anal. Chem. 1983, 55, 1761.

The shutter grid 1 utilized in the present invention may be a conventional Bradbury-Nielson ion shutter which includes an array of parallel wires that are alternately biased. When alternate wires are at equal potentials, ions arriving at the shutter grid are transmitted to the drift region 3. When alternate wires are at unequal potentials, ions arriving at the shutter grid 1 are neutralized and entry into the drift region 3 is prevented. Typically, the shutter grid 1 is pulsed on the 1–50 millisecond time scale, preferably every 40 milliseconds, to transmit ions.

In a preferred embodiment, a thin-ring ion shutter may be utilized in place of the conventional Bradbury-Nielson shutter. The thin-ringed ion shutter is shaped in the form of two conventional drift rings from 1–20 mm in thickness and separated from 0.1–2 mm with an insulator. The shutter 1 will be operated using a fast electronic switch to temporarily eliminate a potential barrier which is created at the thin-ring ion shutter. During the decrease in the potential barrier, ions are permitted to pass the shutter. The electronic switch is flexible for selectively controlling the ion pulse width.

Once the ions pass the shutter grid 1 they travel into the drift chamber 3 and advance to the collector plate 5 under the influence of an accelerating potential field gradient. The collector plate 5, which may be a Farraday plate may also include an aperture grid 12. At the collector plate 5, the ions arrive as ion current peaks separated by arrival times and are sensed electronically by by detector means 13, which may include a high-gain electrometer amplifier. The signal arriving at the detector means 13 via the coaxial cable 31 may be signal averaged in a one-grid mode or recorded on an x-y plotter in a two-grid mode. In one embodiment, detector means 13 includes a microprocessor analyzing the signals arriving at the detector utilizes and determines peak areas instead of peak heights from the IMS spectra to correlate concentrations of analytes in the IMS. Once an IMS spectrum is obtained and stored digitally, a computer algorithm is used to find the nominal baseline, the peak maximum and to integrate the area under the peak. The collector plate 5 is a Faraday detector made of stainless steel. The current arriving at the collector plate 5 is transmitted to a highgain amplifier in the detector means 13 via coaxial coupling means 31. Microprocessors are commercially available to analyze the amplified signal received by the detector plates. In one embodiment signals are amplified by a Keithley Model 427 picoammeter with additional variable amplification of $10^3$ using a high-speed operational amplifier. Signals are processed through digital signal averaging using an Apple IIe modified with Applescope (RC Electronics, Santa Barbara, Calif.). Applescope is a commercially available package of hardware and software for collection and averaging of repetitive signals G. Rico, G. A. Eiceman, C. D. Leasure and V. J. Vandiver, Anal. Instrum., 13 (1984) 289. Generally, 500 scans are acquired per spectrum.

The measurement of pulse area can be compared to the concentration of analyte in the IMS for better correlation to concentration than is possible using pulse heights. The peak heights are affected by the shape of the peak while the peak areas are not affected by peak shape thereby providing the better correlation. Thus, quantitive analysis is realized.

In another embodiment, the components and electronics necessary for operation of the ion mobility spectrometer of the present invention are constructed using a planar printed circuit board which is formed into a cylinder. Various parts of the IMS are fashioned from the elements and wire designs on the printed circuit board. The tube formed from the PC board is designed to connect to the aperture grid, ion shutter, detector plate and repeller plate. All other electronics including filters divider network, microprocessor and shutter control are placed directly on the PC board during initial fabrication. The use of a wrap-around PC board in an IMS will provide low cost and ease of fabrication. The high cost of precision machining of parts required by the prior art IMS design is thereby eliminated.

The choice of material for the wrap-around IMS PC board is such that the material must be flexible, resist high temperatures and have low off-gasing properties.

Presently, ion sources 7 for IMS devices typically use a cylinder of nickel with Ni-63 plated on the inner surface. Ni-63 is used for the formation of positive ions of organics such as benzene, toluene and polycylic aromatic hydrocarbons as well as nitrogen containing compounds such as $NH_2$ and hydrazines. Negative ions may also be formed, in this case from compounds such as pesticides, $NO_x$, $SO_x$, HCl and chlorinated aromatics. The cylinder of nickel is usually 1 to 2 cm in diameter and 1 to 2 cm long. This surface has an area approximately from 2 to 5 square centimeters. Based on this parameter, activities of the ion sources for IMS are in the range from 8 to 12 mCi. A higher activity using these sources becomes difficult because of the self-absorption for more than one layer of Ni-63. One major limitation inherent to IMS is that a very narrow linear range of response of concentration occurs. The limitation on the linear response range has been attributed to a limited availability of ions from the ion source. In an illustrative embodiment of the present invention, the use of a nickel slug approximately 3 to 5 cm in diameter with a plurality of holes for Ni-63 plating is provided. In this embodiment, the source has a much higher surface area and activity rate without requiring an increase in the size of the ion source. This higher activity will increase the linear range of the IMS making the instrument more useful as an atmospheric sensor.

Figure 3:
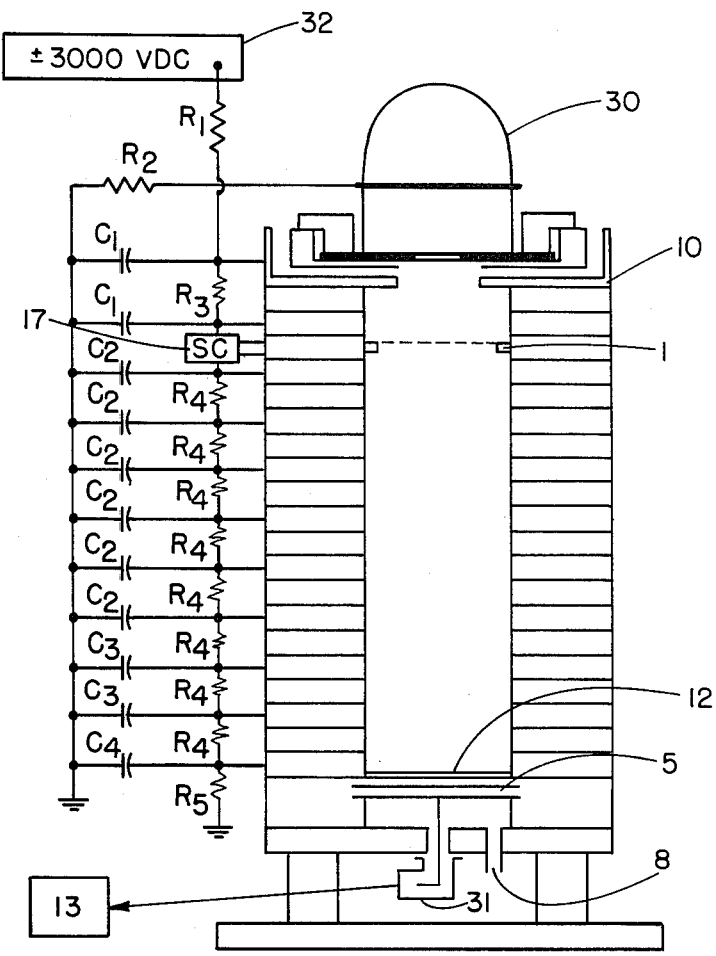
FIG. 3 is a schematic diagram of an ion mobility spectrometer with a hydrogen discharge lamp for photoionization in air.
Figure 3:
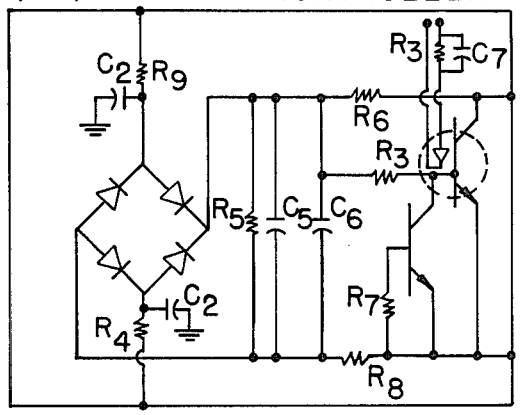

In another embodiment illustrated in FIG. 3, a photoionization lamp 30 is mounted to the repeller plate 10 of the IMS tube to be used as the ion source in place of a radioactive source 7 of FIG. 1. Incorporated herein by reference is the article "Photoionization in Air With Ion Mobility Spectrometry Using a Hydrogen Discharge Lamp" by C. S. Leasure, M. E. Fleischer, G. K. Anderson and G. A. Eiceman (Anal. Chem. 58, 1986, 2142-2147). In this embodiment, the sample is introduced either with the drift gas or into the reaction region 2. The use of a photoionization lamp 30 improves the linear range of the IMS by ionizing substances by a different physical process than the radioactive source. Moreover, the photoionization source changes the selectivity of the instrument to enable the detection of substances different than with the use of a standard Ni-63 Sovig. A hydrogen discharge lamp produces photons at a wavelength of 123.9 nm which can be transmitted in air for short distances before attenuation from absorption of energy from oxygen and water. Using the placement of a source and the resultant drift gas flow characteristics, this lamp can ionize substances for IMS in air in addition to the conventional use of the lamp with nitrogen, even though the lamp produces vacuum ultraviolet light. Substances which form positive ions in the presence of a photoionization source include benzene, toluene, xylene and polycyclic aromatic hydrocarbons.

FIG. 3 further presents the arrangement of the resistors and capacitors utilized with direct gaseous photoionization by a 10.2 eV hydrogen discharge lamp 30. The values of the resistors and capacitors are as follows: $R_1$, 59 K$\Omega$; $R_2$, 1.8 M$\Omega$; $R_3$, 220 K$\Omega$; $R_4$, 240 K$\Omega$; $R_5$, 470 K$\Omega$; $R_6$, 18 K$\Omega$; $R_7$, 15 K$\Omega$; $R_8$, 20 K$\Omega$; $R_9$, 110 K$\Omega$; $C_1$, 0.0047 uF, 6 KV; $C_2$, 0.002 uF, 6 kV; $C_3$, 0.005 uF, 4 kV; $C_4$, 0.47 uF, 600 V; $C_5$, 0.1 mF, 500 V; $C_6$, 4 mF, 450 V; $C_7$, 0.047 uF.

In yet another embodiment, lasers are used as an ionization source in the IMS tube for the characterization of surfaces. In this case the sample may be introduced with the drift gas or between the repeller plate and the shutter grid. The laser source is capable of forming positive ions of surfaces composed of stainless steel, nickel, copper, iron, aluminum, glass, quartz, ceramics, synthetics, teflon, aluminum silicates, polyethylene, polystyrene, butadiene, and plastics. The lasers ionize substances from the surface into the vapor state and are then analysed by the IMS. In this embodiment, the IMS device is designed for the introduction of a variety of surfaces into the instrument. Several factors are important to the operation of the instrument, such as precise control of the sample and position, size and transition of the laser beam, precise control of the laser wavelengths and control of the entrance of created ions into the drift region of the IMS.

Present technology for a characterization of surfaces has two major drawbacks, principally, the majority of instruments for surface characterization can obtain only elemental information about the organic molecules on surfaces, and the majority of these techniques require a high vacuum in order to operate. In addition, none of these techniques are very good for surfaces that are relatively complex, meaning ones that contain more than one compound. Use of laser ionization IMS eliminates some of these drawbacks since IMS operates at atmospheric pressure and can separate and identify mixtures and molecular information.

The IMS device having the laser ionization source would be useful in detection of pesticides from surfaces of plant leaves. In addition, the detection of adsorbed organic materials such as solvents on electronic chips, chemical agents on surfaces in battlefields, molecules adsorbed on catalysts causing poisoning of the catalyst. Forensic analyses are further uses of the laser ion source IMS.

The ion mobility spectrometer of the present invention can separate and detect trace amounts of substances in air that can be utilized in automatic computer control of other devices such as valves, fans and alarms. The computer would use concentration levels of particular substances in a computer algorithm to control the operation of these other devices. The IMS would therefore be interfaced within an overall scheme for computer control of even more devices which would be activated or deactivated based on the results from the IMS. In this system, the IMS could be used for industrial process control and control of automated emergency measures for military or civilian industrial applications. Moreover, a grid array of IMS devices could map the movement of a plume of toxic gas with computer prediction of future movement or dispersal for evacuation procedures.

The grid array system is comprised of a central computer which is connected to several remote data collection microprocessors which are each interfaced with up to 16 ion mobility spectrometers. Each IMS operates as an atmospheric point sensor for continuous detection and identification of trace amount of substances in air. The number of remote data collection microprocessors can be as many as 16. Thus, a response from up to 256 IMS devices that are independent and self-supporting can be monitored using a single central computer.

The IMS units maybe either fixed site or mobile in design. Graphic display from the central computer will be used to portray the total system condition in real time or simply a response from a single IMS. Responses may also be stored for later retrieval and reconstruction of events causing a response in an IMS within the array. Additional modifications of the central computer may be made to include alarms, medical information based on IMS response and stored toxilogical information and predictions on movement of a chemical plume across the array region. The grid array system may be useful for many applications including manufacturing plants where releases of toxic material in the atmosphere are possible, sites where potentially hazardous material is stored and population centers near a site where toxic material is manufactured or stored.

Furthermore, the IMS spectrometer may be utilized as a personal monitoring device. A small IMS device is strapped to an individual for use as a monitor for collection of personal exposure data. A portable power supply is used and data is stored either in RAM, magnetic tape or computer disk since all data is digital. Moreover, if required, a constant readout and/or alarm is included. The IMS of the present invention is uniquely suited for use as a personal monitor. The IMS is an extremely sensitive and selective sensor for substances that may be toxic to humans. The entire unit weighs between five and ten pounds. In addition, the IMS is a direct reading continuous monitor wherein data is collected almost instantaneously. The device is especially helpful in complying with OSHA regulations as a direct reading instrumentation to avoid the need to take repetitive samples to evaluate compliance with ceiling standards on substances. The invention is useful in applications such as for industrial companies concerned with worker exposure to potentially toxic substances, military uses for similar concerns and for use by OSHA personnel for testing for worker exposure to insure compliance of regulations.

While illustrative embodiments of the subject invention have been described and illustrated, it is obvious that various changes and modifications can be made therein without departing from the spirit of the present invention which should be limited only by the scope of the appended claims.

What is claimed is:

1. An ion mobility spectrometer comprising:
    a substantially cylindrical spectrometer tube having an ion shutter within said tube defining a reaction chamber and a drift chamber, both of said chambers being at atmospheric pressure, said drift chamber including a plurality of metallic rings concentrically aligned and extending from the ion shutter to a first end of the spectrometer tube, said first end having a collector plate and an inlet in communication with ambient air;

detector means in communication with said collector plate for detecting and analyzing the drift velocity of ions arriving at said collector plate;

means for applying a potential gradient across the tube;

means for applying a potential gradient across said ion shutter;

means for producing product ions from a sample within said reaction chamber; and means for causing air to pass through said inlet into said drift chamber and reaction chamber;

whereby said air entering through said inlet acts as both a sample and carrier gas that undergoes molecular reactions in the reaction chamber to produce product ions and said air also acting as a drift gas that collides with the product ions passing through said ion shutter into the drift chamber causing said product ions to arrive at the collector plate having a drift velocity detected and analyzed by said detector means.

2. The ion mobility spectrometer of claim 1 further comprising insulators between the metallic rings of the drift chamber.

3. The ion mobility spectrometer of claim 1 further comprising O-rings between the metallic rings of the drift chamber.

4. The ion mobility spectrometer of claim 1 further comprising a lining throughout the inner diameter of the drift tube.

5. The ion mobility spectrometer of claim 4 wherein the lining is a glass tube with segments on the outside of the glass tube for receiving the metallic rings.

6. The ion mobility spectrometer of claim 4 wherein the lining is comprised of teflon.

7. The ion mobility spectrometer of claim 1 or 4 wherein the detector means also includes a microprossesor to analyze signals by peak areas.

8. The ion mobility spectrometer of claim 1 wherein the means for producing product ions includes a radioactive source.

9. The ion mobility spectrometer of claim 1 wherein the inlet comprises a sample inlet and a carrier gas inlet.

10. The ion mobility spectrometer of claim 9 wherein the carrier gas inlet includes a molecular sieve cartridge.

11. The ion mobility spectrometer of claim 9 wherein the carrier gas inlet includes a variable flow controller.

12. The ion mobility spectrometer of claim 1 wherein the means for causing air to pass through said inlet into said drift chamber and reaction chamber includes pump means located at a second end of said spectrometer tube opposite said first end.

13. The ion mobility spectrometer of claim 12 where the pump means is coupled to a gas outlet means at said second end of said spectrometer tube.

14. The ion mobility spectrometer of claim 8 wherein the radioactive source is Ni-63.

* * * * *